United States Patent
Dougherty et al.

[11] 3,941,478
[45] Mar. 2, 1976

[54] SECOND HARMONIC ANALYZER

[75] Inventors: Joseph Patrick Dougherty, Ossining; Stewart K. Kurtz, Yorktown Heights; Robert John Seymour, Ossining, all of N.Y.

[73] Assignee: North American Philips Corporation, New York, N.Y.

[22] Filed: Mar. 24, 1975

[21] Appl. No.: 555,199

[52] U.S. Cl. .................... 356/30; 356/51; 250/226; 250/578
[51] Int. Cl.² ........................................ G01N 21/00
[58] Field of Search ........... 250/222, 552, 339, 578, 250/226; 356/206, 239, 30, 31, 51; 331/94.5 N

[56] References Cited
UNITED STATES PATENTS

| | | | |
|---|---|---|---|
| 2,802,947 | 8/1957 | Hamacher | 250/31 X |
| 3,407,309 | 10/1968 | Miller | 331/94.5 N X |

OTHER PUBLICATIONS

Kurtz et al., Journal of Applied Physics, Vol. 39, No. 8, pp. 3798–3813, July 1968.

Primary Examiner—Walter Stolwein
Attorney, Agent, or Firm—Frank R. Trifari; Carl P. Steinhauser

[57] ABSTRACT

A method and device for determining acentricities in a powder material by illuminating the powder with a collimated coherent light beam of given wave-length which generates a second harmonic in the material. The second harmonic with the fundamental removed by filters is divided by a beam splitter and sent to two photomultipliers — one of which has a narrow band filter to select only light of one wave-length. If all the light is generated at the second harmonic equal signals are produced by the photomultipliers. If non-second harmonic radiation is produced, a larger signal will be produced in the unfiltered reference channel.

10 Claims, 4 Drawing Figures

SECOND HARMONIC ANALYZER

This invention relates to a method and device for determining acentricities in a powder sample. In particular the invention is useful in measuring potential electrooptic materials, and determining the absence of a crystallographic center of symmetry. The method basically consists of irradiating a sample with a high-power laser at a frequency ω and measuring the power generated at the second harmonic at a frequency 2 ω.

A technique and device for evaluating non-linear optical materials has been described in an article entitled "A Powder Technique For The Evaluation of Non-Linear Optical Materials" by S. K. Kurtz and T. T. Perry published in The Journal of Applied Physics, Vol. 39, No. 8, pp. 3798–3813 (July, 1968). Further work has shown that a detection sensitivity of at least $10^{-3}$ of the harmonic from a quartz powder standard is required to establish whether a material is acentric or centric at a high (99 percent) confidence level. This requires working at nominal laser power densities of $10^4$ to $10^5$ W/cm$^2$ which normally should not give rise to unwanted visible optical signals variously referred to in the literature as burning, plumes and laser damage. The fact is, however, that in a powder these or similar effects occur at the power levels shown to be essential for reliable center of symmetry determination. This has limited the reliability of this method to date in detecting acentricity to about that of the Giebe-Schiebe powder test. Detection of such very small acentricities is important in crystal structure determinations as well as the study of disorder near phase transitions.

It is an object of our invention to provide a method of determining whether a material is acentric or centric at a high confidence level.

This and further objects of the invention will appear as the specification progresses.

According to the invention a flash lamp pumped Nd:Glass laser ($\lambda$=1.06 $\mu$m) with an optical energy of 1 joule and a pulse length of 300 $\mu$s is used in single pulse operation. After the flash lamp radiation is removed by a filter, the beam is focused on a powdered sample. If the sample is crystallographically acentric, the second harmonic (2ω) of the laser fundamental frequency (ω) will be generated. After the fundamental is removed by filters, this second harmonic light (SHG) is divided by a beam splitter and sent to two filters to select out the green (5300A) SHG light. This dual channel system is specially designed so that when all the light collected from the sample has wave-length $\lambda$=5300A (SHG), balanced signals will be displayed on an oscilloscope from the two photomultipliers. This is accomplished by means of a beam splitter which splits the light by a ⅓, ⅔ ratio. The ⅓ portion goes directly to a photomultiplier. The ⅔ portion is directed through a narrow pass filter with 50 percent transmission at the second harmonic wave-length before it arrives at a second photomultiplier. The signals from the photomultipliers are only equal if all the light produced is at the SHG wave-length.

The dual channel presentation is unbalanced if any of the visible light is produced by laser damage mechanisms since in this case a larger signal will be detected in the unfiltered reference channel. This technique allows one to achieve the required sensitivity of $10^{-3}$ quartz required for high reliability while simultaneously guarding against spurious signals. Thus, the detector assembly is carefully designed by the judicious combination of standard optical components so that it functions as a single wave-length spectrometer of high collection efficiency.

An additional unique feature of the system is the use of an optimum solid angle for collecting the second harmonic light at the photomultipliers. When the powders are immersed in a liquid having an index refraction equal to the crystal at the second harmonic, then the second harmonic light is collected with a high efficiency. An added benefit is a noticeable decrease in the spurious radiation for a given laser intensity.

The invention will be described with reference to the accompanying drawing in which.

Figure 1:
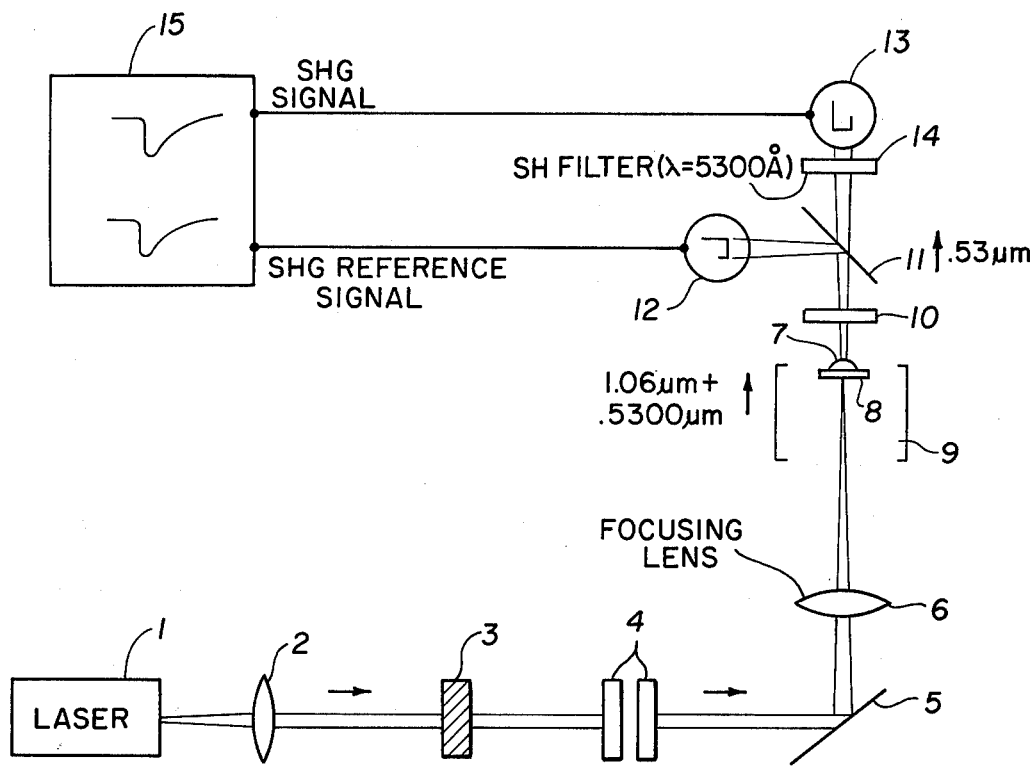
FIG. 1 shows a block diagram of the second harmonic analyzer.

As shown in FIG. 1, a neodymium glass laser 1 produces, when energized, a flash of visible light together with infra-red at a wavelength of 1.06 $\mu$m which is collimated by a lens 2. Visible light is removed by filter 3 leaving only 1.06$\mu$ and other infra-red radiation which is attenuated by neutral density filters 4 which is reflected by a mirror 5 and focussed by a lens 6 onto a sample 7 on a sample holder 8 in a sample chamber 9.

If the sample is crystallographically acentric, the second harmonic (2ω) of the laser fundamental frequency (ω) will be generated, i.e., a second harmonic at 0.53 $\mu$m will be generated. After the fundamental and other infra-red radiation is removed by filter 10, this second harmonic (SHG) is divided by a beam splitter 11 and sent to two photomultipliers 12 and 13.

Figure 2:
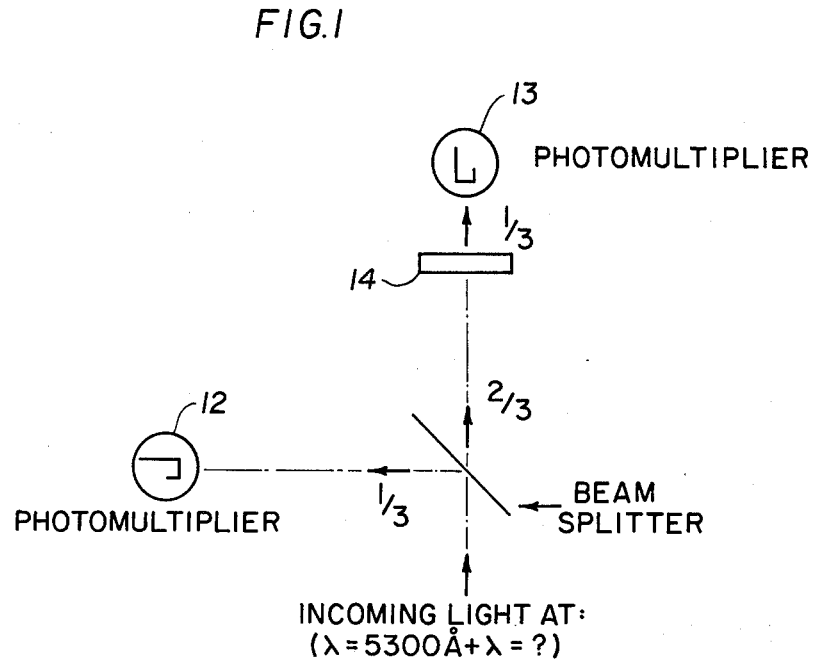
FIG. 2 shows a sectional view of the analyzer.

The incident radiation on the beam splitter is divided so that one third is directed to photomultiplier 12 (see FIG. 2) while two-thirds is passed to photomultiplier 13. Between the beam splitter and photomultiplier 13 a narrow pass filter 14 having a 50 percent transmission at 0.53$\mu$ ± 150A is provided. Thus, if only the second harmonic is present, only one-third of the incoming light from the sample is received by photomultiplier 13.

The signals from each of the photomultipliers are displayed conveniently on an oscilloscope 15, the signal from photomultiplier 12 being a reference signal. When all the light collected from the sample has a wave-length $\lambda$=5300A (SHG), balanced signals will be displayed on the oscilloscope from the two photomultipliers.

The dual channel presentation is unbalanced if any of the visible light is produced by laser damage mechanisms since in this case a larger signal will be detected in the unfiltered reference channel.

Figure 3:
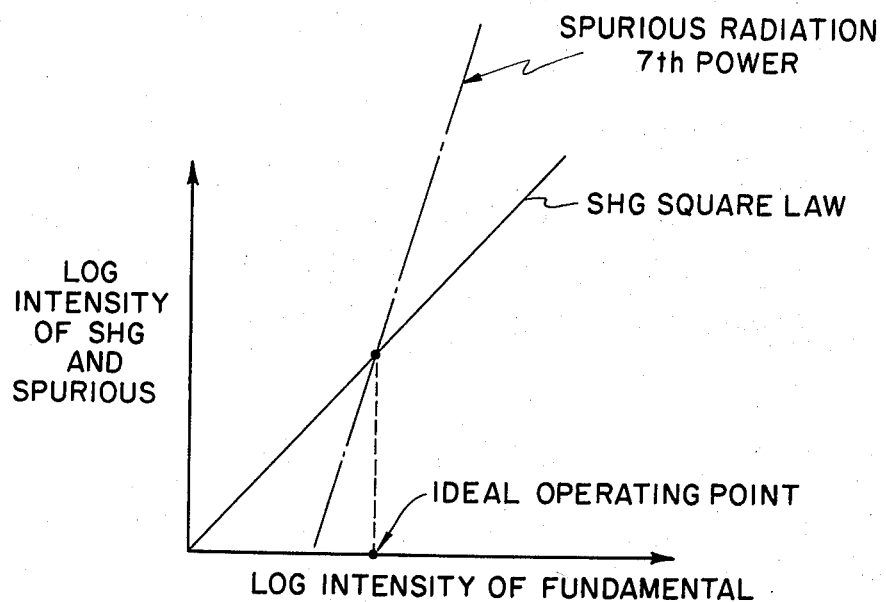
FIG. 3 shows the relationship between the signal intensity and attenuation.

For optimum detection of SHG the power density of the laser at the powder cannot be arbitrarily increased. FIG. 3 shows the SHG and spurious signals as a function of attenuation (neutral density) in the laser beam for several different laser beam diameters (at the powder). It is clear that an optimum focussing of the beam exists. For the 1 joule, 300$\mu$s laser used, this optimum is close to 3mm. diameter at the powder sample.

Figure 4:
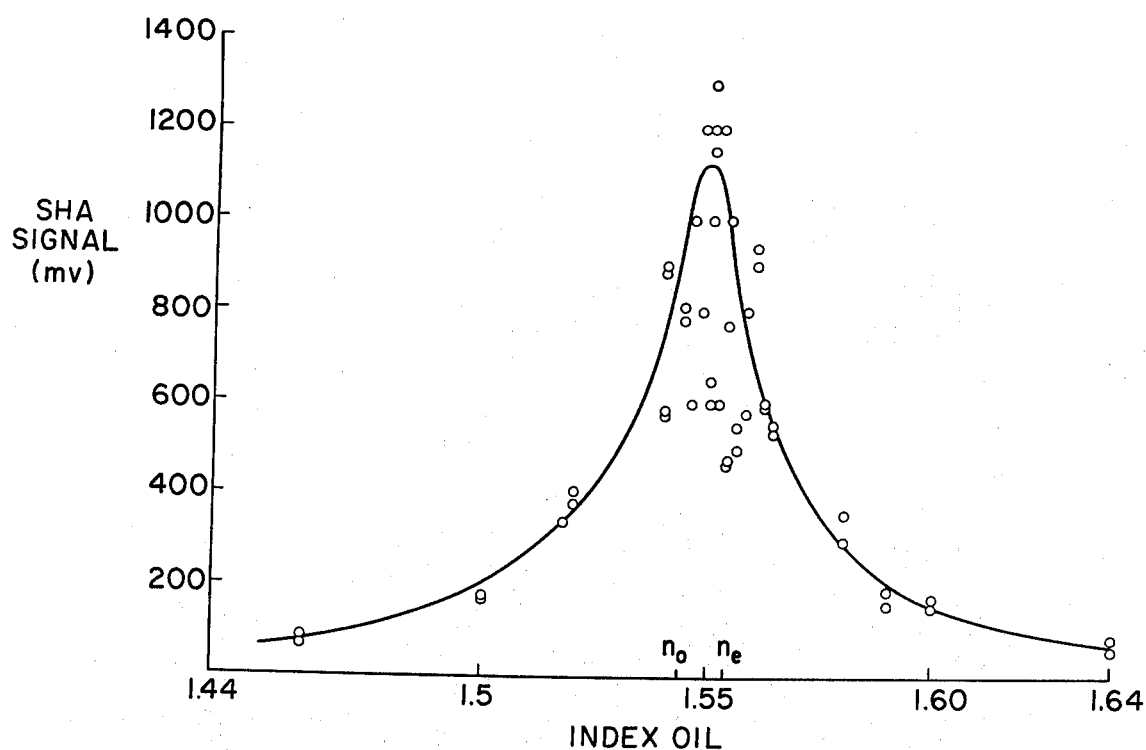
FIG. 4 shows the relationship of the second harmonic intensity as a function of refractive index mismatch.

An additional unique feature of the system is the use of an optimum solid angle for collecting the second harmonic light at the photomultipliers. When the powders are immersed in a liquid having an index refraction equal to the index of the crystal at the second harmonic, then the second harmonic light is collected with a high efficiency. An added benefit is a noticeable decrease in the spurious radiation for a given laser intensity. A plot of second harmonic intensity versus refractive index mismatch is shown in FIG. 4 for the quartz reference. The optimum collection solid angle is achieved when the active area of the photomultiplier cathode is filled by the second harmonic beam from an index matched powder. The high sensitivity of this optical configuration to refractive index mismatch ($\Delta n$'s of 0.02 can be readily detected), as shown in FIG. 4, provides a practical means for identification of the material responsible for the second harmonic generation. This is an important feature not available in other nonlinear optical configurations. It combines in a single function both second harmonic generation and refractive index identification of the particular compound (for instance in a mixture) which is generating the harmonic. It is distinct (in giving more information) than the conventional immersion (Becke line) methods of optical crystallography which provide no means of distinguishing centric from acentric compounds. For instance, in a mixture of two materials A and B, the normal immersion method could determine the indices of refraction of A and B separately. Conventional SHG as disclosed in the earlier publication could only say that A or B (or both) are acentric if SHG was observed. In the present analyzer, we can determine which component is acentric (or also both) if that is the case by varying the index of the immersion oil and and find the peak in the second harmonic intensity. This is especially important in mineralogical and industrial samples where unwanted impurities (including dirt) may get in the powders and give a misleading result.

What is claimed is:

1. A method of determining crystallographic acentricities in a powder sample comprising the steps of exposing the powder sample to a beam of collimated coherent radiation of given fundamental wave-length and intensity to generate the second harmonic of said radiation in said sample, removing the fundamental from the radiation after the sample to leave only the second harmonic, dividing the second harmonic into two separate beams one of which has a greater intensity than the other, the beam of lesser intensity serving as a reference beam, passing the beam of greater intensity through a filter having a narrow passband to limit said latter beam to the second harmonic only, reducing the intensity of said latter beam to balance said beams at the second harmonic frequency, detecting and displaying the intensities of each of said beams, and comparing the intensities of the respective beams to thereby determine acentricities in the powder sample.

2. A method as claimed in claim 1 in which the sample is placed in a liquid having a given index of refraction producing a maximum signal intensity.

3. A method as claimed in claim 2 in which the sample is immersed in a liquid having an index of refraction substantially equal to the crystal at the second harmonic.

4. A method as claimed in claim 3 in which the radiation is pulsed.

5. A method as claimed in claim 4 in which the pulse length is 300$\mu$s.

6. A device for determining crystallographic acentricities in a powder sample comprising a source of coherent radiation of a given fundamental wave-length and intensity, means to position the sample in the path of said radiation to expose the sample thereto, means to remove the fundamental after passage through the sample leaving essentially only a second harmonic of the fundamental, means to divide the beam after the sample into two beams, a narrow pass filter in the path of one of the beams to limit the frequency in said beam to substantially only the second harmonic, means to balance the intensities of the two beams at the second harmonic frequency, means in the path of each of said divided beams to detect the intensity thereof, and means to display the relative intensities of said beams to thereby determine acentricities in the sample.

7. A device as claimed in claim 6 in which the sample is immersed in a liquid having a given index refraction producing a maximum signal intensity.

8. A device as claimed in claim 7 in which the liquid has an index of refraction substantially equal to the crystal at the second harmonic.

9. A device as claimed in claim 8 in which the radiation source is a flash lamp pumped Nd:Glass laser.

10. A device as claimed in claim 6 in which the narrow pass filter has a 50 percent transmission characteristic at the second harmonic frequency and said dividing means has a one-third to two-thirds beam intensity ratio.

* * * * *